United States Patent
Steinbach et al.

(10) Patent No.: US 6,350,472 B1
(45) Date of Patent: *Feb. 26, 2002

(54) METHOD OF TREATING HIV INFECTION WITH TRANSDERMAL GEL CONTAINING MAMMALIAN LIVER EXTRACT

(75) Inventors: Thomas Steinbach, Houston; Phillip R. Pylant, Katy; William J. Hermann, Jr., Sealy, all of TX (US)

(73) Assignee: Steinbach, Pylant, and Hermann, L.L.C., Sealy, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/210,401

(22) Filed: Dec. 14, 1998

(51) Int. Cl.[7] .................... A61K 35/407; A61K 35/12; A61K 38/00
(52) U.S. Cl. .................. 424/553; 424/520; 514/12; 514/21
(58) Field of Search .................. 424/553, 106, 424/78, 285, 251, 270, 256, 520; 530/399; 514/885, 12, 21

(56) References Cited

U.S. PATENT DOCUMENTS

| | | | | |
|---|---|---|---|---|
| 4,254,103 A | | 3/1981 | Timar | 424/106 |
| 4,474,753 A | * | 10/1984 | Haslam et al. | 424/78 |
| 4,883,660 A | | 11/1989 | Blackman et al. | 424/78 |
| 5,055,296 A | * | 10/1991 | Wagle et al. | 424/553 |
| 5,284,664 A | | 2/1994 | Wagle et al. | 424/553 |
| 5,316,775 A | | 5/1994 | Wagle et al. | 424/553 |
| 5,334,395 A | | 8/1994 | Wagle et al. | 424/553 |
| 5,492,937 A | | 2/1996 | Bogentoft et al. | 514/781 |
| 5,589,192 A | | 12/1996 | Okabe et al. | 424/486 |
| 5,595,760 A | | 1/1997 | Cherif-Cheikh | 424/464 |
| 5,770,209 A | * | 6/1998 | Grotendorst et al. | 424/198.1 |
| 5,846,955 A | * | 12/1998 | Pidgeon et al. | 514/77 |

FOREIGN PATENT DOCUMENTS

| | | | | |
|---|---|---|---|---|
| CA | 2084331 | * | 6/1993 | 424/553 |

OTHER PUBLICATIONS

Stedman's Medical Dictionary, 26th Ed. pp. 1325, 1995.*
Chase, "Doctors and Patients Hope AZT Will Help Stave Off AIDS," *Wall Street Journal,* Apr. 28, 1988, pp. 1 and 19.

* cited by examiner

*Primary Examiner*—Jean C. Witz
*Assistant Examiner*—Patricia Patten
(74) *Attorney, Agent, or Firm*—Fitzpatrick, Cella, Harper & Scinto

(57) ABSTRACT

A method for treating human immuno-deficiency virus infection (HIV-1), comprising administering a therapeutically effective amount of a mammalian liver extract characterized by being heat stable, insoluble in acetone, and soluble in water. A transdermal colloidal dispersion delivery system for use in the treatment of HIV-1 infection further comprises an emulsion of resolubilized, concentrated mammalian liver extract.

9 Claims, No Drawings

METHOD OF TREATING HIV INFECTION WITH TRANSDERMAL GEL CONTAINING MAMMALIAN LIVER EXTRACT

BACKGROUND OF THE INVENTION

1. Field of the Invention

The present invention is directed to a method of treating human immuno-deficiency virus (HIV-1) infections and to the discovery that a mammalian liver extract is efficacious in treating such infections. The present invention is also directed to a method of treating HIV-1 infections with this same mammalian liver extract. The present invention is further directed to a method of preparing a colloidal dispersion for use with this same mammalian liver extract. The present invention is also directed to a method of using a transdermal colloidal dispersion delivery system to treat HIV-1 infections.

2. Brief Description of Prior Art

Acquired immune deficiency syndrome (AIDS) and AIDS-related complex (ARC) are caused by human immuno-deficiency virus (HIV-1), a retrovirus. The HIV-1 virus infects immune, neural, and other cells of its host. Eventually most people infected with HIV-1 become abnormally susceptible to a variety of serious opportunistic diseases as a result of the immune deficiency caused by the virus.

The current anti-HIV-1 drugs are either not effective or cause undesirable side effects. These drugs include AZT, 2',3'-dideoxy cytidine (ddCyd), interferon (IFN), mismatched double stranded RNA (dsRNA) and amphotericin B. In particular, AZT, which has shown some promise in the treatment of AIDS, causes very serious side effects, such as bone marrow suppression, in a high proportion of patients. Also, the beneficial effects of AZT have been reported to abate in 12–18 months, and patients get new infections or develop toxic side effects. (Chase, "Doctors and Patients Hope AZT Will Help Stave Off AIDS," *Wall Street Journal*, Apr. 28, 1988, p. 14, col. 1.)

One commercially available mammalian liver abstract useful for purposes of the present invention is sold under the trademark KUTAPRESSIN by Kremers-Urban Co., of Milwaukee, Wis. According to product literature, this extract exerts its action only with respect to tissues that have been injured, and particularly when inflammation and edema are present.

U.S. Pat. No. 5,055,296, filed by certain inventors common to the present application further discloses use of a particular heat stable, acetone-insoluble, water-soluble mammalian liver extract, designated as "KU 10,001" that was shown to be effective in the treatment of mammals infected with a non-dermatological virus and, in particular, chronic fatigue syndrome. The disclosure of this patent as to such extracts are incorporated herein by reference. This patent also discloses preliminary results of this extract as a protector of MT-2 cells using an in vitro test culture, when exposed to HIV-1.

U.S. Pat. No. 5,284,664, filed by certain inventors common to the present application, disclose a heat stable, acetone-insoluble, water-soluble mammalian liver extract, that is said to be effective in the treatment of symptoms of Alzheimer's Disease. The liver extract was also partially sequenced, and that sequence listing is incorporated herein by reference.

U.S. Pat. No. 5,316,775, filed by certain inventors common to the present application, discloses the same mammalian liver extract and demonstrates it to be effective in the treatment of Hepatitis B infections.

U.S. Pat. No. 5,334,395, filed by certain inventors common to the present application, discloses use of the same mammalian liver extract and demonstrates it to be effective in the treatment of Epstein-Barr viral infections.

U.S. Pat. No. 4,254,103, discloses a method of extracting Hepatoprotector Factor (HF) from bovine liver to be used in the treatment of cirrhosis of the liver and viral hepatitis.

U.S. Pat. No. 4,883,660, discloses gel bases for use in pharmaceutical compositions comprising a glycol solvent, and ethoxylated fatty alcohols or ethoxylated behenyl alcohol. The composition is suitable for topical, systemic and oral administration of pharmaceutical agents.

U.S. Pat. No. 5,492,937, discloses a composition which is a liquid at or below room temperature, and forms a highly viscous gel at body temperature. This composition is comprised of a cellulose ether, a surfactant, and other optional additives. It may be used for oral or local administration of a pharmaceutical to the skin, mucous membrane, eye, or body cavity.

U.S. Pat. No. 5,589,192, discloses a gel formulation for use with local anesthetics. A support of non-woven fabric with an impervious backing sheet is coated with a copolymer containing a local anesthetic. A polymer/drug matrix is formed, and an aqueous fluid is used to coat the surface of the matrix, converting the matrix into a gel with good percutaneous absorption.

U.S. Pat. No. 5,595,760, discloses a composition which includes a soluble, gelable salt of a peptide, and a pharmaceutical carrier. The composition forms a gel upon interacting with body fluids after injection, and the peptides are released continuously over a period of at least three days.

Against this background, the inventors have endeavored to discover a method to treat HIV-1 infections, using a heat stable, acetone-insoluble, water-soluble mammalian liver extract.

SUMMARY OF THE INVENTION

The present invention provides a method of treating HIV-1 infections involving administering to a mammal having said disease a therapeutically effective amount of mammalian liver extract, the extract being characterized by being heat stable, insoluble in acetone, and soluble in water. The terminology "heat stable" means that the liver extract does not lose appreciable activity at temperatures of about 100° C. in water over ten minutes. A preferred extract is specifically referred to as KUTAPRESSIN, which is further concentrated as disclosed herein. Also, this invention relates to a method of preparing a transdermal colloidal dispersion delivery system for use with said mammalian liver extract. This invention further relates to a method of using a transdermal colloidal dispersion delivery system to treat HIV-1 infections. One advantage of the above-mentioned colloidal dispersion delivery system is the improved ease of administration of the pharmaceutical composition by the patient. Another advantage of the above-mentioned colloidal dispersion delivery system is the ability to provide the pharmaceutical composition in a concentration high enough to be therapeutically effective in the treatment of HIV-1 infections.

Another advantage of the invention is the highly concentrated nature of the liver extract. The extracts of the prior art were more dilute and therefore administration of the liver extracts at dosages shown to be therapeutically effective herein for the treatment of HIV-1 viral infections was difficult and inefficient.

DETAILED DESCRIPTION OF PREFERRED EMBODIMENTS

The portion of mammalian liver extract that has been discovered to be effective in treating HIV-1 infection is the fraction which is heat stable, insoluble in acetone, and soluble in water. As disclosed in U.S. Pat. Nos. 5,284,664, 5,316,775, and 5,334,395, it is believed that these polysaccharides are present in KUTAPRESSIN in the form of proteoglycans or glycoproteins.

A transdermal delivery system has been discovered to be a particularly effective method of delivering a mammalian liver extract, such as KUTAPRESSIN, when further concentrated according to the present invention. Such a transdermal delivery system allows the concentrated liver extract to be absorbed into the blood in concentrations apparently adequate for the treatment of HIV-1 infection.

Preparation of a Transdermal Colloidal Dispersion Delivery System for Kutapressin The transdermal colloidal dispersion employed in the present invention is one of the preferred methods for administering the liver extract.

A soy lecithin gel is prepared from 10 grams of soy lecithin, to which 11.7 ml of isopropyl palmitate and 0.2 g of sorbic acid are added. The gel is then allowed to meld for 24 hours. A 20% poly(oxypropylene)-poly(oxyethylene) copolymer gel, such as Pluronic 127 (BASF), is prepared by adding 0.2 g of potassium sorbate and 100 ml of distilled water to 20 g of Pluronic 127. This gel is also allowed to meld for 24 hours.

Dessicated liver extract is used to prepare the gel formulation. One way in which this may be accomplished is described below by dessicating 3 vials (60 ml) of commercially available KUTAPRESSIN. A Nalgene dessicating system is set up using calcium sulfate as the dessicating absorbant. Two evaporating dishes containing the KUTAPRESSIN are placed in the apparatus and a vacuum is applied via a pump for 7 minutes. The dessicating absorbant must be changed every 24 hours, and the vacuum pressure must be reapplied after each change of absorbant to restore the vacuum. After 72 hours, the liquid will be absorbed, leaving only active ingredient.

Six ml of preserved water and 4 drops of phenol are added to the KUTAPRESSIN, and it is allowed to solubilize. This is the resolubilized liver extract preparation. The liquid is placed in a 30 ml syringe attached to another 30 ml syringe by a Luer Lock adapter. Seven ml of soy lecithin gel is added to the solubilized KUTAPRESSIN in the syringe. The liquids are transferred between the two syringes until an emulsion forms. With the syringes still attached and the emulsified liquid in one syringe, 17 ml of 20% Pluronic 127 is added to the empty syringe. The Pluronic 127 is then transferred to the KUTAPRESSIN emulsion. This results in a colloidal dispersion. The colloidal dispersion is then transferred between the syringes about 20 times to further emulsify the mixture. This final colloidal dispersion volume is about 30 ml, and it contains KUTAPRESSIN at a concentration of about 50 mg/ml.

It is also anticipated that a transdermal delivery system comprised of lecithin and other penetration enhancers; vehicles other than lecithin which alter the molecular environment of the epidermis; an adhesive patch containing a drug reservoir, with or without a rate controlling membrane, covered by an occlusive backing; iontophoresis; and phonophoresis may be used to deliver the liver extracts of the present invention.

Administration of Liver Extract

An acetone-insoluble liver extract useful in the present invention preferably is administered percutaneously, for example, using a transdermal colloidal dispersion delivery system in the form of a patch applied to the skin, or by applying the colloidal dispersion directly to the skin. However, other forms of administration are contemplated.

The liver extract may be employed in the form of pharmaceutically acceptable salts of the components, such as alkali metal salts. The pharmaceutically acceptable amides, lower alkyl esters, protected derivatives, other derivatives and analogs of the components of the liver extract are also contemplated.

While a transdermal colloidal dispersion formulation is preferred, other pharmaceutical carriers, for example, a saline solution, could be employed. The liver extract preferably is administered percutaneously while contained in a colloidal dispersion. A preferred product is a colloidal dispersion comprised of any of a variety of transdermal delivery vehicles and penetration enhancers containing KUTAPRESSIN which has been concentrated to a level of about 50 mg/ml. Iontophoretic and phonophoretic methods of introducing KUTAPRESSIN transdermally are also contemplated.

Dosages may vary depending upon the condition of the patient. Generally, however, it has been found that the administration of 400 mg of KUTAPRESSIN per day will produce beneficial results in as little as about 4 weeks.

CLINICAL OBSERVATION EXAMPLE 1

A patient infected with HIV-1 received 400 mg of KUTAPRESSIN percutaneously daily. Administration of the percutaneous colloidal dispersion composition was begun after Quantitative HIV RNA PCR analysis was used to determine the number of HIV RNA copies per ml of the patient's blood. The initial level of HIV RNA was documented as 18,000 copies/ml.

After receiving 400 mg of KUTAPRESSIN daily for 4 weeks, quantitative HIV RNA PCR analysis revealed that the patient's HIV RNA level dropped to 6,400 copies/ml. The dosage of KUTAPRESSIN was then lowered to 200 mg per day percutaneously. The patient's blood was tested to determine the HIV RNA level after approximately 10 weeks of treatment at this dosing level. The level of HIV RNA present was documented as 14,400 copies/ml.

Although the invention has been described previously in connection with special and preferred embodiments, it will be understood that it is capable of modification without departing from the scope of the invention. The following claims are intended to cover all variations, uses, or adaptations of the invention which follow, in general, the principles thereof and including any departures from the present disclosure that are within known or customary practices in the field to which this invention pertains, or as are obvious to persons of ordinary skill in the field.

We claim:

1. A method of treating an HIV-1 infection in a mammal by administering percutaneously, through a topical application to the skin, a therapeutically effective amount of a porcine liver extract in a colloidal dispersion through a composition comprised of:

a transdermal delivery system comprising a colloidal dispersion containing a lecithin and a copolymer gel; and a therapeutically effective amount of a porcine liver extract in said colloidal dispersion, wherein said porcine liver extract is at a concentration of about 50 mg/ml in said dispersion, and further comprises a heterogeneous polypeptide mixture that is heat stable, insoluble in acetone, soluble in water and is also referred to as Kutapressin, that has been concentrated to substantially remove liquid and then emulsified to form said dispersion, so that said porcine liver extract is present in said transdermal delivery system in concentrated form as a dispersion, and substantially at least 400 mg of the porcine liver extract thereby is topically administered daily.

2. The method of claim 1, wherein the colloidal dispersion delivery system includes phophatidylcholine.

3. The method of claim 1, wherein the phophatidylcholine is present in the composition as soy lecithin.

4. The method of claim 1, wherein the transdermal colloidal dispersion delivery system includes poly(oxypropylene)-poly(oxyethylene).

5. The method of claim 1, wherein the transdermal delivery system is administered directly to the skin.

6. The method of claim 1, wherein the transdermal delivery system is administered in the form of a skin patch.

7. The method of claim 1, wherein the transdermal delivery system is iontophoresis.

8. The method of claim 1, wherein the transdermal delivery system is phonophoresis.

9. A method for treating HIV-1 infections comprising administering percutaneously, through a topical application to the skin of a mammal having said infection, a therapeutically effective amount of a porcine liver extract in a colloidal dispersion containing a lecithin and a copolymer gel, wherein said porcine liver extract is at a concentration of about 50 mg/ml in the dispersion, and further comprises a heterogeneous polypeptide mixture that is heat stable, insoluble in acetone, soluble in water and is also referred to as Kutapressin, that has been concentrated to substantially remove liquid and then emulsified to form said dispersion, so that said porcine liver extract is present in said dispersion in a concentrated form and substantially at least about 400 mg of the porcine liver extract thereby is topically administered daily.

* * * * *